(12) United States Patent
Kurtock et al.

(10) Patent No.: US 7,208,119 B1
(45) Date of Patent: Apr. 24, 2007

(54) HOSPITAL METER SYSTEM

(75) Inventors: James R. Kurtock, Fishers, IN (US); Sandy M. Richards, Pershing, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 09/516,758

(22) Filed: Mar. 1, 2000

(51) Int. Cl.
 *G01N 33/48* (2006.01)
(52) U.S. Cl. .................. 422/61; 422/58; 422/68.1; 422/82.05
(58) Field of Classification Search ............. 422/58, 422/61, 68.1, 82.05; 436/43–44, 166
See application file for complete search history.

(56) References Cited

U.S. PATENT DOCUMENTS

| | | |
|---|---|---|
| 3,970,996 A | 7/1976 | Yasaka et al. |
| 4,871,258 A | 10/1989 | Herpichboehm et al. |
| 5,011,290 A | 4/1991 | Terada et al. |
| 5,160,980 A | 11/1992 | Herpichboehm et al. |
| 5,232,668 A | 8/1993 | Grant et al. |
| 5,232,796 A * | 8/1993 | Baumgartner ............... 429/187 |
| 5,246,858 A | 9/1993 | Arbuckle et al. |
| 5,284,770 A | 2/1994 | Adrian et al. |
| 5,332,549 A * | 7/1994 | MacIndoe, Jr. .............. 422/63 |
| 5,366,609 A | 11/1994 | White et al. |
| 5,371,687 A | 12/1994 | Holmes et al. |
| 5,379,214 A | 1/1995 | Arbuckle et al. |
| 5,508,171 A | 4/1996 | Walling et al. |
| 5,522,255 A | 6/1996 | Neel et al. |
| 5,572,873 A | 11/1996 | Lavigne et al. |
| 5,594,906 A | 1/1997 | Holmes et al. |
| 5,686,659 A | 11/1997 | Neel et al. |
| 5,710,622 A | 1/1998 | Neel et al. |
| 5,787,839 A * | 8/1998 | Magnant et al. ........... 119/51.5 |
| 5,789,664 A | 8/1998 | Neel et al. |
| 5,792,944 A | 8/1998 | Lennert et al. |
| 5,832,921 A | 11/1998 | Lennert et al. |

(Continued)

FOREIGN PATENT DOCUMENTS

JP 02055033 2/1990

(Continued)

OTHER PUBLICATIONS

Supplemental 510(k) Notification for Glucometer II Improved Blood Glucose Meter, Miles Laboratories, Inc., Jun. 10, 1986.

*Primary Examiner*—Lyle A. Alexander
(74) *Attorney, Agent, or Firm*—Barnes & Thornburg LLP

(57) ABSTRACT

A healthcare data management system for use with an instrument for determining the concentration of a medically significant component of a body fluid. The instrument includes a first port. The system includes a cradle for receiving the instrument. The cradle includes a second port for coupling to the first port to download data from the instrument to the cradle. The apparatus further includes a base having a third port. The cradle includes a fourth port for coupling to the third port to permit downloading to the base of data collected from the instrument by the cradle. The apparatus further includes an accessory box including a fifth port. Engagement of the cradle with the accessory box couples the fourth and fifth ports. Engagement of the accessory box with the base couples the third and fifth ports.

11 Claims, 11 Drawing Sheets

U.S. PATENT DOCUMENTS

| | | |
|---|---|---|
| 5,841,023 A | 11/1998 | Parker et al. |
| 5,865,745 A | 2/1999 | Schmitt et al. |
| 5,929,422 A * | 7/1999 | Lappe .................. 235/462.13 |
| 6,830,731 B1 * | 12/2004 | Buechler et al. .............. 422/82 |

FOREIGN PATENT DOCUMENTS

| | | |
|---|---|---|
| JP | 02055034 | 2/1990 |
| WO | WO 94/13198 | 6/1994 |
| WO | WO 94/24929 | 11/1994 |
| WO | WO 00/07013 | 2/2000 |

* cited by examiner

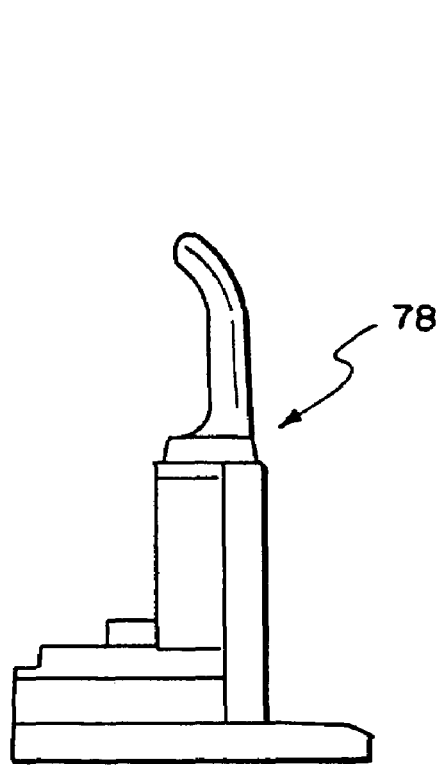
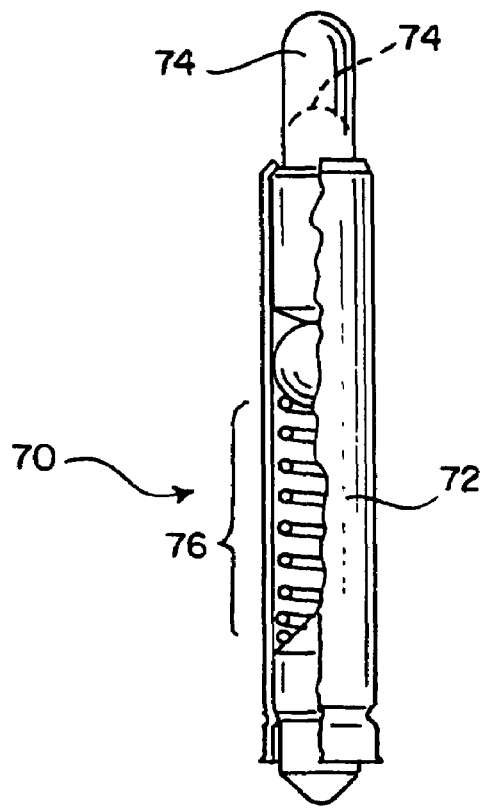
FIG. 3          FIG. 7
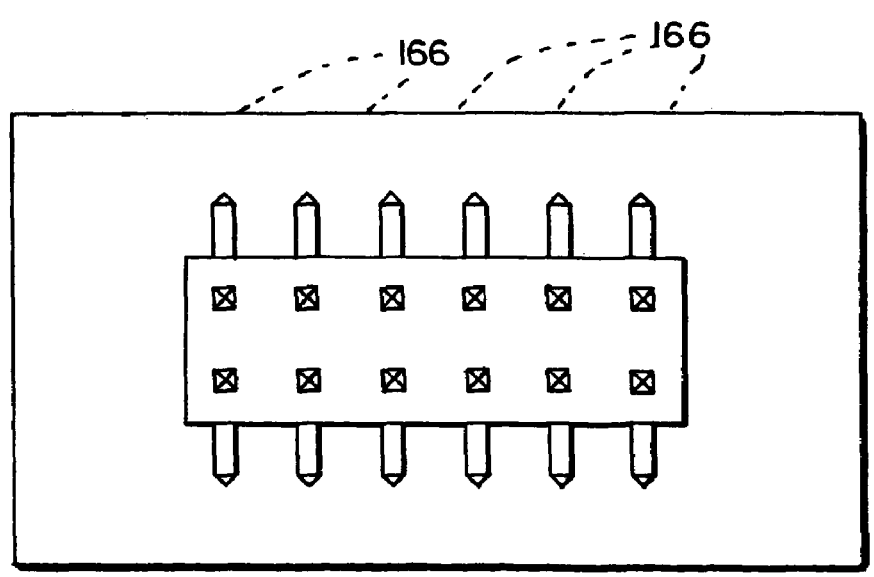
FIG. 8

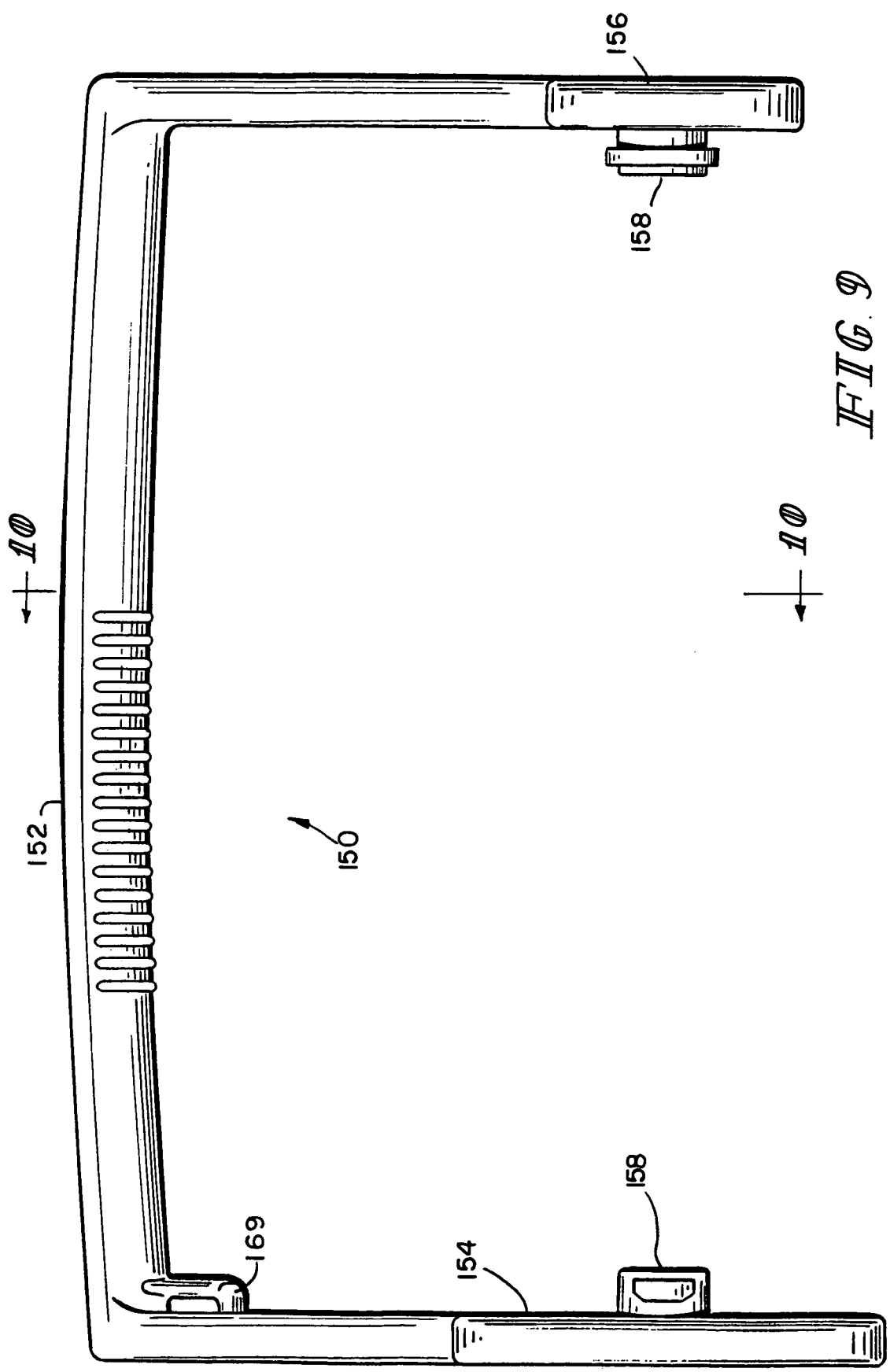

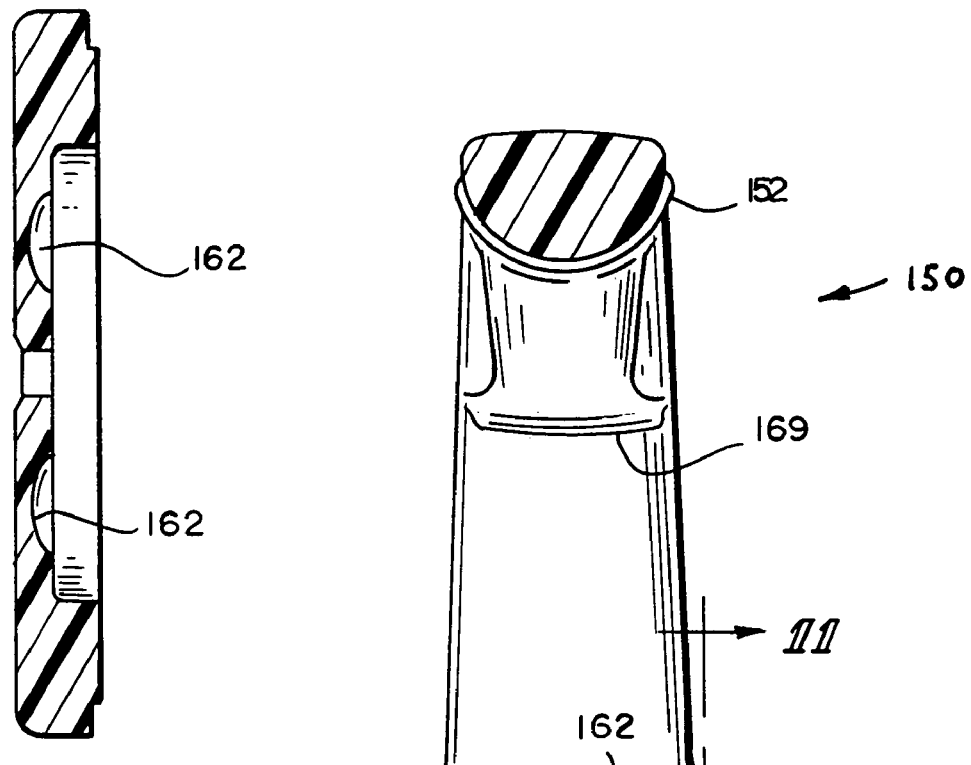
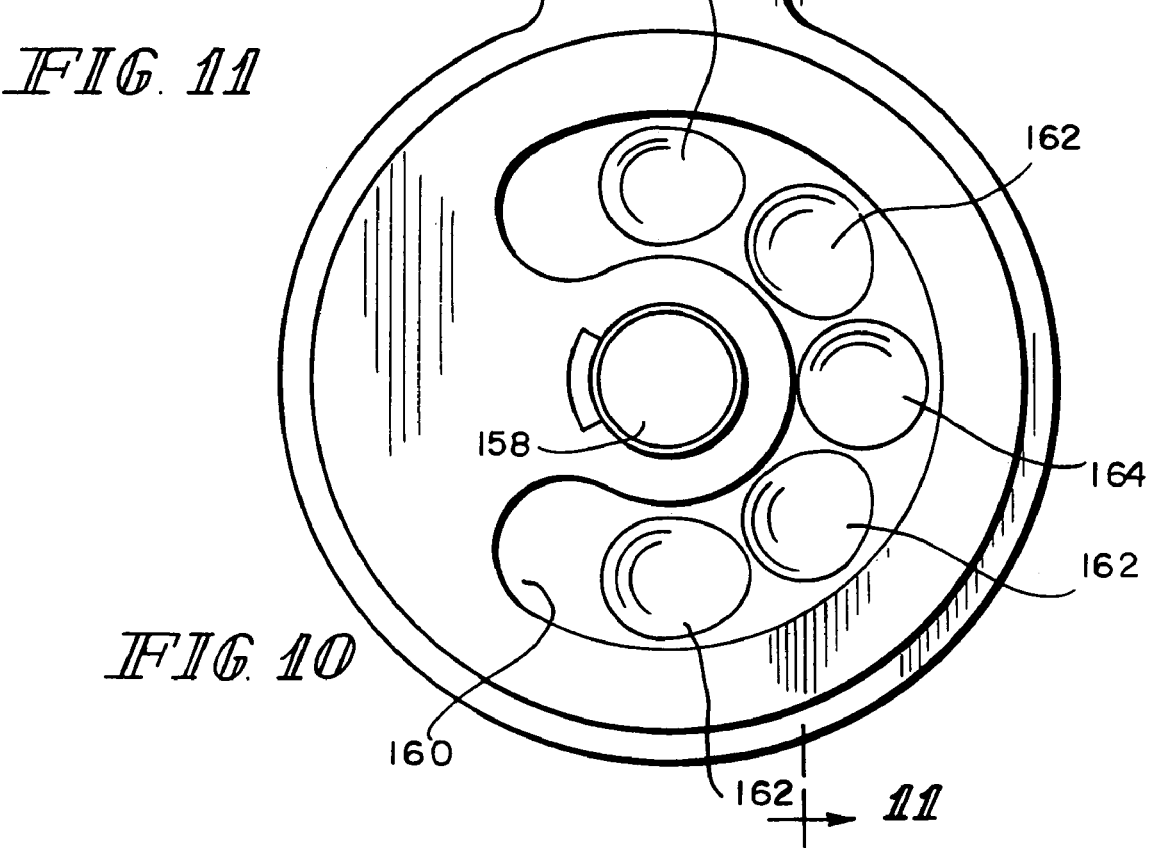

HOSPITAL METER SYSTEM

CROSS-REFERENCE TO RELATED APPLICATIONS

Reference is hereby made to U.S. design patent application 29/101,237, titled CRADLE FOR INSTRUMENT filed Mar. 1, 1999, and assigned to the same assignee, U.S. design patent application 29/101,236, titled ACCESSORY BOX FOR CRADLE FOR INSTRUMENT filed Mar. 1, 1999, and assigned to the same assignee, and U.S. design patent application 29/101,274, titled BASE FOR CRADLE FOR INSTRUMENT OR FOR ACCESSORY BOX FOR CRADLE FOR INSTRUMENT filed Mar. 1, 1999, and assigned to the same assignee, all of which are hereby incorporated herein by reference.

FIELD OF THE INVENTION

This invention relates to hospital and health care facility data management. It is disclosed in the context of a blood glucose data management system, but is believed to be useful in other applications as well.

BACKGROUND OF THE INVENTION

Various systems for the acquisition and management of health care data are known. The systems described in the following listed U.S. patents are illustrative only, and are by no means intended to be an exhaustive listing of the known types of systems: U.S. Pat. Nos. 4,871,258; 5,011,290; 5,160,980; 5,232,668; 5,246,858; 5,284,770; 5,366,609; 5,379,214; 5,371,687; 5,508,171; 5,594,906; 5,522,255; 5,686,659; 5,710,622; 5,789,664; 5,792,944; 5,832,921; and 5,841,023. The disclosures of these patents are hereby incorporated herein by reference.

DISCLOSURE OF THE INVENTION

Illustratively, according to the invention, a data acquisition and management system is provided for downloading health care data, for example, glucose concentrations in bodily fluids such as blood, determined by, and stored in, instruments such as, for example, Roche Diagnostics Corporation's Accuchek® Advantage™ and Accuchek® Complete™ hand-held blood glucose monitoring instruments. Such an instrument typically includes a first input/output (I/O) port for the entry of, for example, instructions and operating parameters into the instrument, and the downloading of data from the instrument to a host, such as, for example, a system of the type described in the above-identified U.S. Pat. Nos. 5,371,687 and 5,594,906. The system keeps track of the identities of the instruments from which it receives data. In this way, the system can, for example, identify the data with a particular patient to whom a particular instrument is assigned.

According to the one aspect of the invention, a healthcare data management system is provided for use with an instrument for determining the concentration of a medically significant component of a body fluid. The instrument includes a first port. The system includes a cradle for receiving the instrument. The cradle includes a second port for coupling to the first port to download data from the instrument to the cradle.

Illustratively according to this aspect of the invention, the cradle further includes means for the entry of data by an operator. Illustrative data entry means include touch screens and/or key pads for the manual entry of data.

Further illustratively according to this aspect of the invention, the system includes a base. The base includes a third port and the cradle includes a fourth port. Coupling of the third and fourth ports permits downloading to the base of data collected from the instrument by the cradle.

Additionally illustratively according to this aspect of the invention, coupling of the third and fourth ports includes providing complementary surfaces on the cradle and base. Engagement of the complementary surfaces of the cradle and base couples the third and fourth ports.

Illustratively according to this aspect of the invention, the cradle includes at least one rechargeable battery for powering circuitry in the cradle. The base includes a power supply. Coupling of the third and fourth ports permits charging of the battery from the power supply.

Further illustratively according to this aspect of the invention, the base includes a fifth port for coupling to a port on a computer to permit transmission of data from the base to the computer.

Additionally illustratively according to this aspect of the invention, the system includes a computer for storing and/or analyzing and/or generating reports based upon the data. The base includes a fifth port for coupling to a sixth port on the computer.

Illustratively according to this aspect of the invention, the system includes a bar code reader. The system is capable of reading bar code from patient identification devices to identify data which is entered into the system with a particular patient.

Additionally or alternatively illustratively according to this aspect of the invention, the system is capable of reading bar code from operator identification devices to identify data which is entered into the system with a particular operator.

Illustratively according to this aspect of the invention, the bar code reader is incorporated into the cradle.

Further illustratively according to this aspect of the invention, the system includes an accessory box including a seventh port. Engagement of the cradle with the accessory box couples the fourth and seventh ports.

Additionally illustratively according to this aspect of the invention, coupling of the fourth and seventh ports includes providing complementary surfaces on the accessory box and cradle. Engagement of the complementary surfaces of the accessory box and cradle couples the fourth and seventh ports.

Illustratively according to this aspect of the invention, coupling of the third and fourth ports includes providing complementary surfaces on the accessory box and base. Engagement of the complementary surfaces of the accessory box and base couples the third and fourth ports through the seventh port.

Further illustratively according to this aspect of the invention, the accessory box includes a housing and a carrying handle pivotally coupled to the housing.

Additionally illustratively according to this aspect of the invention, the carrying handle has two ends. One of the ends includes a number of yieldable locking positions for the handle with respect to the housing.

Further illustratively according to this aspect of the invention, the handle includes a locking position of the handle with respect to the housing.

Illustratively according to this aspect of the invention, at least one of the handle and the cradle includes a feature for engagement with the other of the cradle and the handle when the cradle engages the accessory box and the handle is in the non-yieldable locking position.

Further illustratively according to this aspect of the invention, the accessory box includes a drawer accessible from two opposite sides of the accessory box. The drawer includes a stop for reducing the likelihood of accidental disengagement of the drawer from the accessory box when the accessory box is withdrawn from either of said two opposite sides.

Additionally illustratively according to this aspect of the invention, the drawer includes latches to reduce the likelihood of inadvertent opening of the drawer.

According to another aspect of the invention, a healthcare data management system for use with an instrument for determining the concentration of a medically significant component of a body fluid includes a cradle for receiving the instrument and an accessory box for receiving the cradle. The accessory box includes a housing and a carrying handle pivotally coupled to the housing. The carrying handle has two ends. One of the ends includes a number of yieldable locking positions for the handle with respect to the housing.

Illustratively according to this aspect of the invention, the handle further includes a non-yieldable locking position with respect to the housing.

Further illustratively according to this aspect of the invention, the handle includes a feature for engagement with the cradle when the cradle engages the accessory box and the handle is in the non-yieldable locking position.

Additionally illustratively according to this aspect of the invention, the accessory box includes a drawer accessible from two opposite sides of the accessory box. The drawer includes a stop for reducing the likelihood of accidental disengagement of the drawer from the accessory box when the accessory box is withdrawn from either of the opposite sides.

Illustratively according to this aspect of the invention, the accessory box includes a drawer accessible from two opposite sides of the accessory box. The drawer includes latches to reduce the likelihood of inadvertent opening of the drawer.

Further illustratively according to this aspect of the invention, one of the ends includes a button which is yieldably urged into engagement with one of a number of depressions which define the yieldable locking positions of the handle.

Additionally illustratively according to this aspect of the invention, said one of the ends further includes an opening which defines a non-yieldable locking position of the handle.

Illustratively according to this aspect of the invention, the bottoms of the depressions are formed to include ramps to permit force on the handle to move the handle among the yieldable locking positions defined by the depressions.

Further illustratively according to this aspect of the invention, the opening includes a sidewall which defines the non-yieldable locking position. The sidewall is configured to permit locking of the handle in the non-yieldable locking position.

Additionally illustratively according to this aspect of the invention, the opening permits access to the button to permit movement of the handle from the non-yieldable locking position.

Illustratively according to this aspect of the invention, at least one of the handle and the cradle includes a feature for engagement with the other of the cradle and the handle when the cradle engages the accessory box and the handle is in the non-yieldable locking position.

BRIEF DESCRIPTION OF THE DRAWINGS

The invention may best be understood by referring to the following detailed description and accompanying drawings which illustrate the invention. In the drawings:

FIG. 3 illustrates a side elevational view of a detail of the component illustrated in FIGS. 1–2, taken generally along section lines 3—3 of FIG. 2;

FIG. 7 illustrates an enlarged, partly sectional side elevational view of a detail of the components illustrated in FIGS. 1–6;

FIG. 8 illustrates an enlarged top plan view of a detail of the component illustrated in FIGS. 5–6;

FIG. 9 illustrates a side elevational view of a detail of the component illustrated in FIGS. 5–6, taken generally along section lines 9—9 of FIG. 5;

FIG. 10 illustrates a sectional view of the detail illustrated in FIG. 9, taken generally along section lines 10—10 of FIG. 9;

FIG. 11 illustrates a sectional view of the detail illustrated in FIGS. 9–10, taken generally along section lines 11—11 of FIG. 10;

DETAILED DESCRIPTION OF AN ILLUSTRATIVE EMBODIMENT

Figure 1:
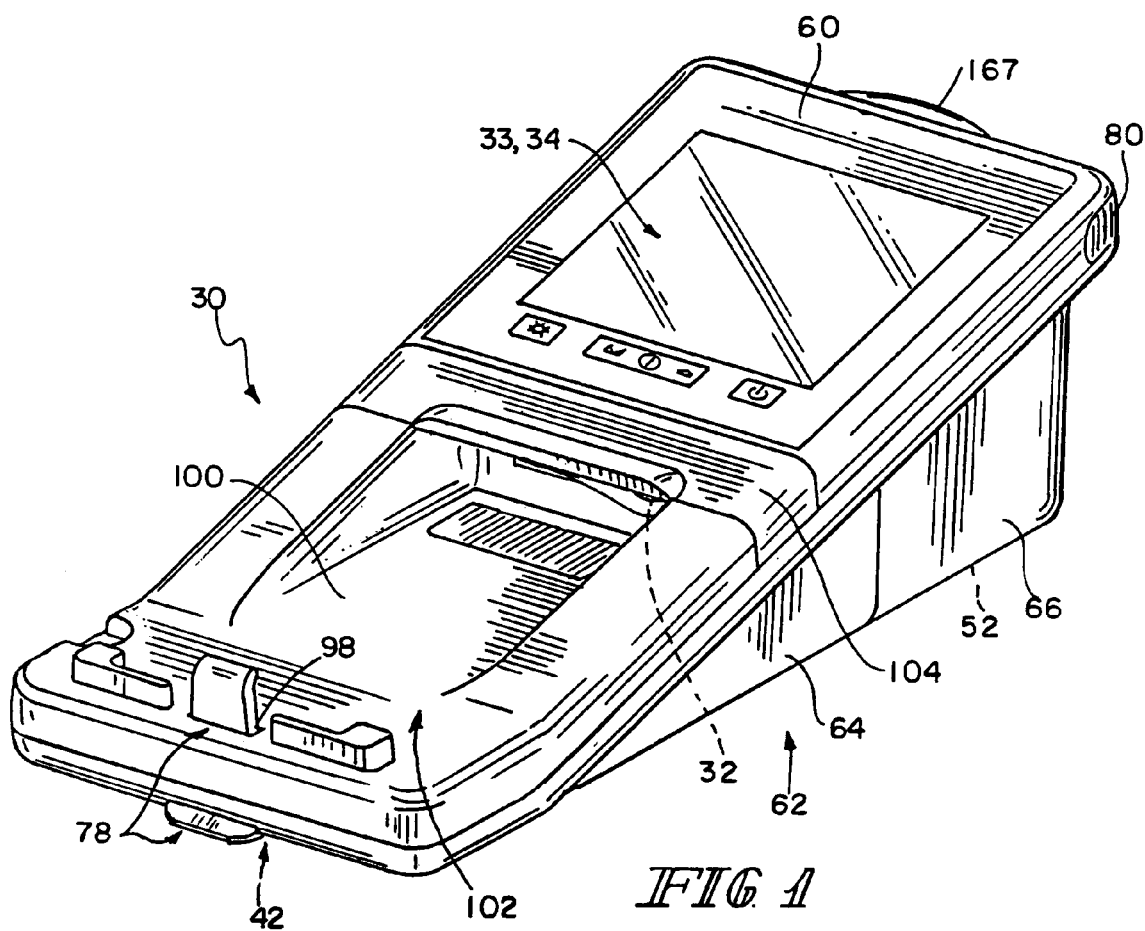
FIG. 1 illustrates a perspective view of a component of a system constructed according to the invention.

Turning now particularly to FIGS. 1–2, 4, 13 and 14, a data acquisition and management system 20 is provided for downloading health care data, for example, glucose concentrations in bodily fluids such as blood, determined by, and stored in, instruments 22 such as, for example, Accuchek® Advantage™ and Accuchek® Complete™ hand-held blood glucose monitoring instruments. Such an instrument 22 typically includes a first, illustratively infrared (1R), input/output (I/O) port 24 for the entry of, for example, instructions and operating parameters into the instrument 22, and the downloading of data from the instrument 22 to a host computer 26 (FIG. 12), such as, for example, a hospital data management system of the type described in the above-identified U.S. Pat. Nos. 5,371,687 and 5,594,906, or the printing of reports directly from the cradle 30 via a printer port on the base 38. The system 20 keeps track of the identities of the patients and/or operators from whom it receives data. In this way, the system 20 can, for example, identify the data with a particular patient and/or with a particular operator who is taking readings/entering data into the system 20.

Figure 12:
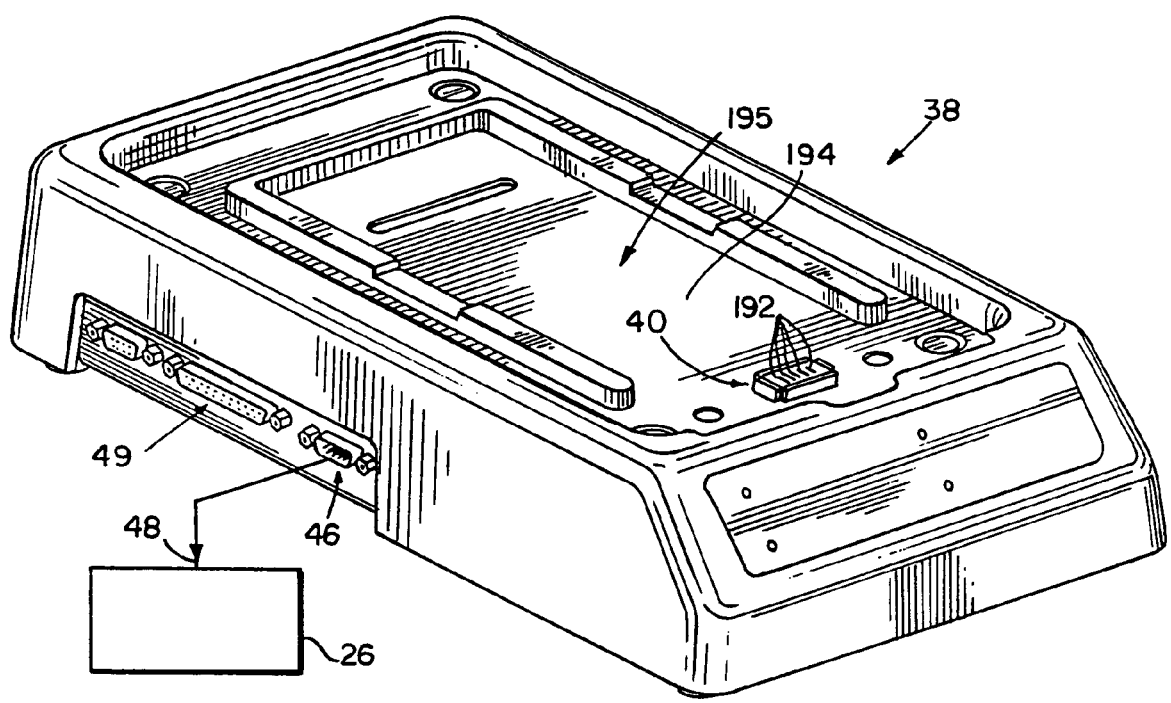
FIG. 12 illustrates a perspective view of a component of a system constructed according to the invention; and, FIGS. 13 and 14 illustrate partly fragmentary perspective views of two systems according to the present invention.
Figure 13:
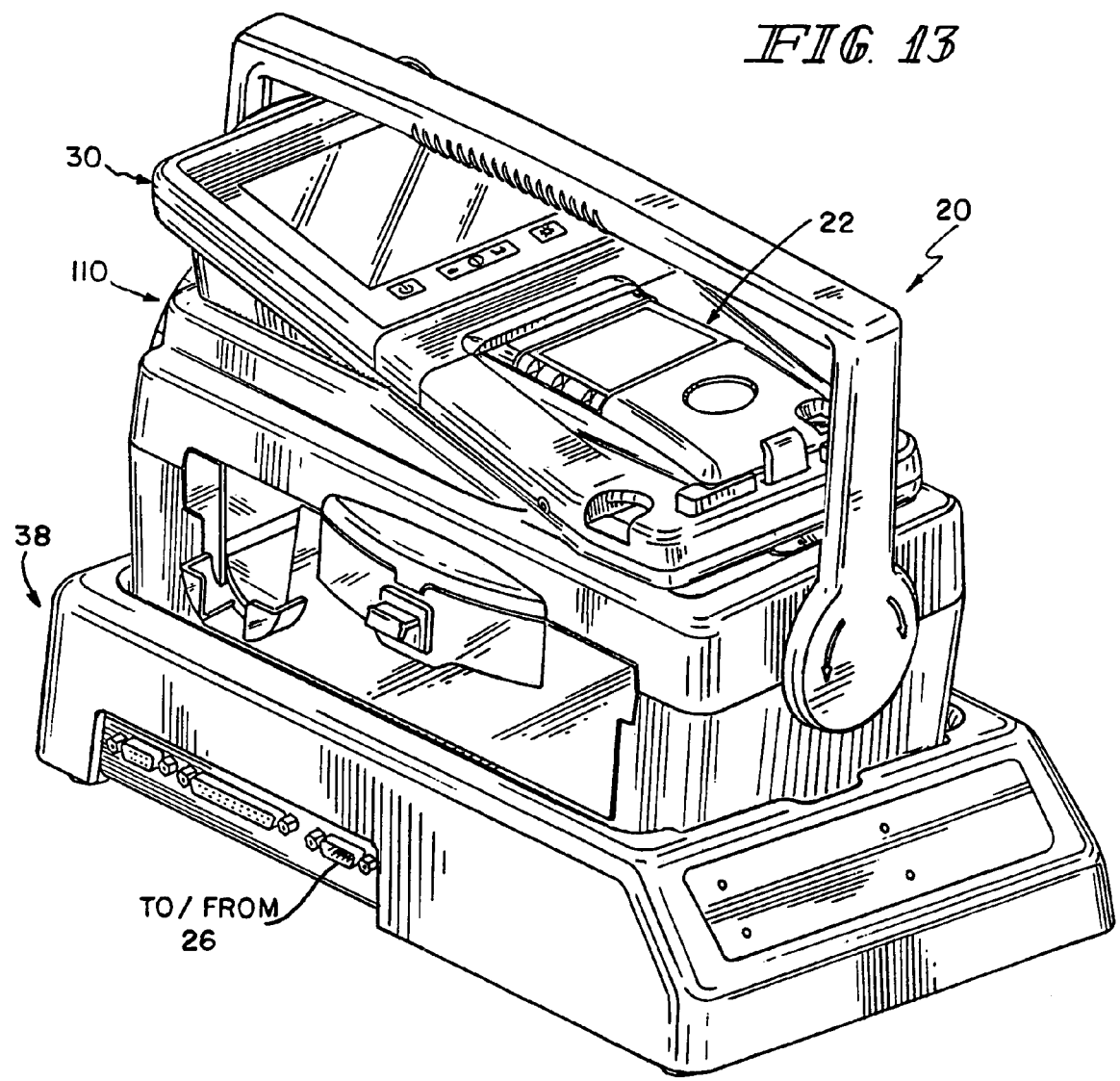
Figure 14:
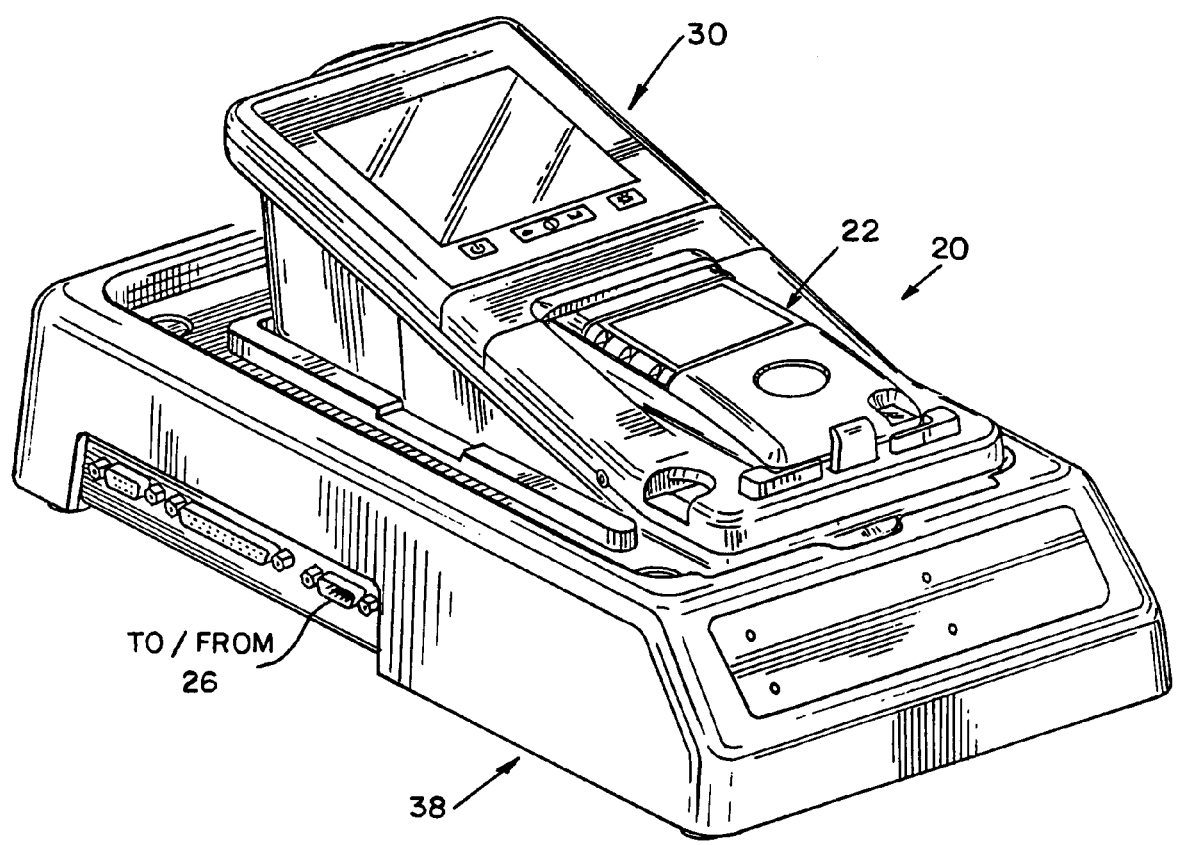

The system 20 includes such an instrument 22 and a cradle 30 for receiving the instrument 22. The cradle 30 may include a second, illustratively, IR, I/O port 32 for coupling to the first port 24 provided on the instrument 22 to download data from the instrument 22 to the cradle 30. The cradle 30 also includes a touch screen 33 and liquid crystal display (LCD) 34, key pad, or the like for the manual entry of data by an operator. The system 20 further includes a base 38 (FIG. 12). The base 38 includes a third port 40 for coupling to a fourth port 42 on the cradle 30. Coupling of the third and fourth ports 40, 42 permits downloading of data from the cradle 30 through the base 38. Coupling of the third and fourth ports 40, 42 permits charging of batteries 44 used to power circuitry 45 in the cradle 30 from a power supply in the base 38. The use of rechargeable batteries 44 reduces the requirement to change batteries. The illustrated base 38 further includes a fifth port 46 for coupling to a port 48 on computer 26 to permit the downloading of data through the base 38 to the computer 26 for storage, analysis and report generation, or for coupling directly to a printer (not shown) for the printing of reports directly from cradle 30. A port 49 in the base 38 permits the base 38 to be coupled directly to a printer (not shown).

Figure 2:
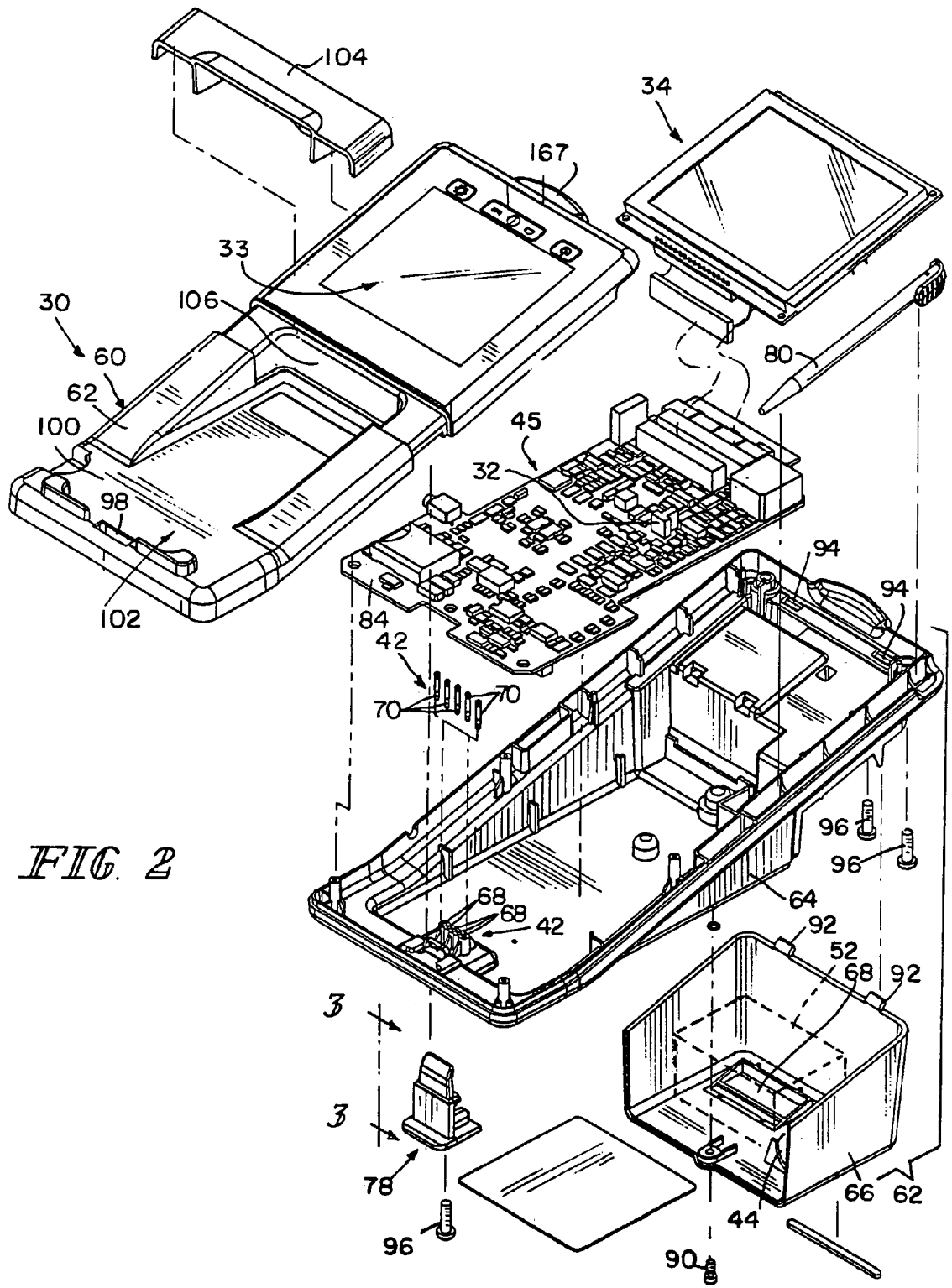
FIG. 2 illustrates a fragmentary exploded perspective view of the component illustrated in FIG. 1.
Figure 4:
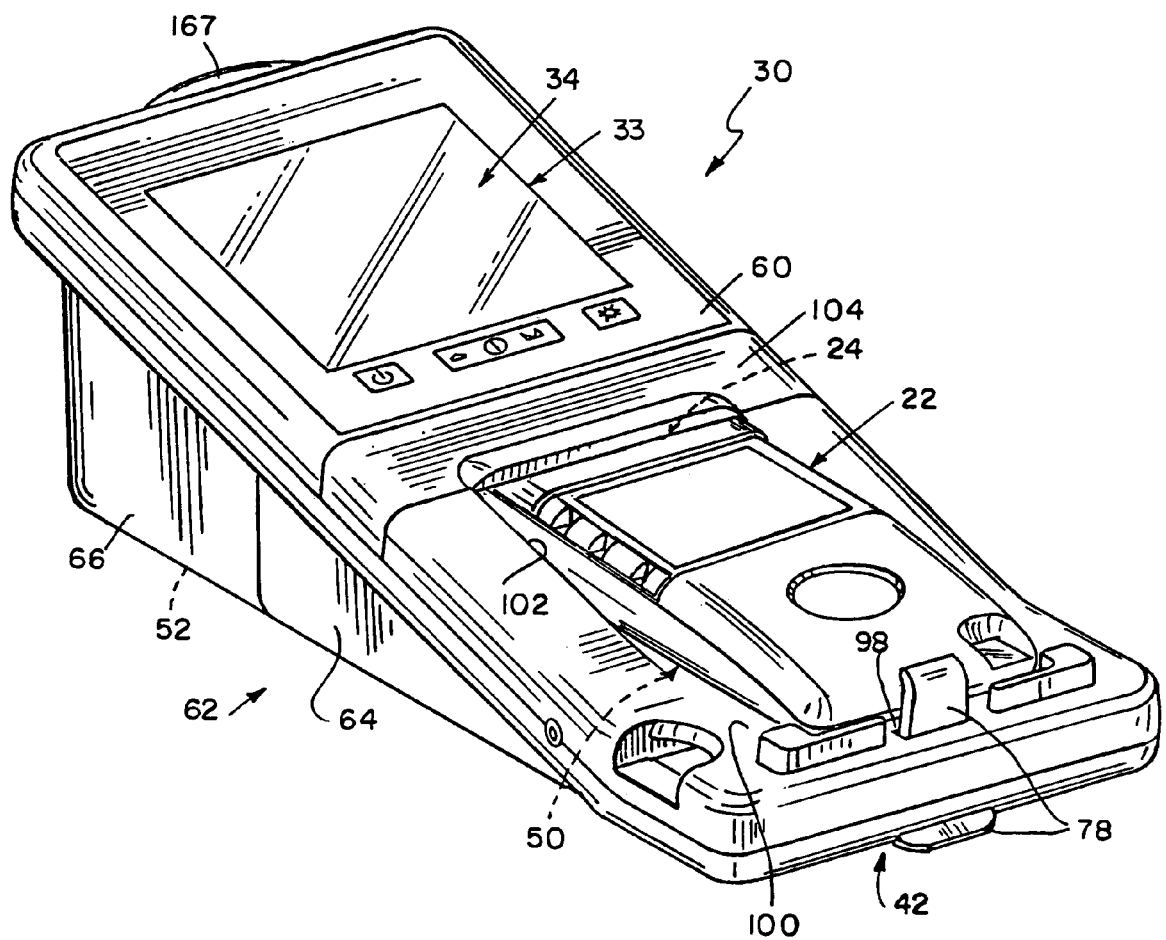
FIG. 4 illustrates a perspective view of a component of a system constructed according to the invention with an instrument for testing for glucose concentration inserted into it.
Figure 5:
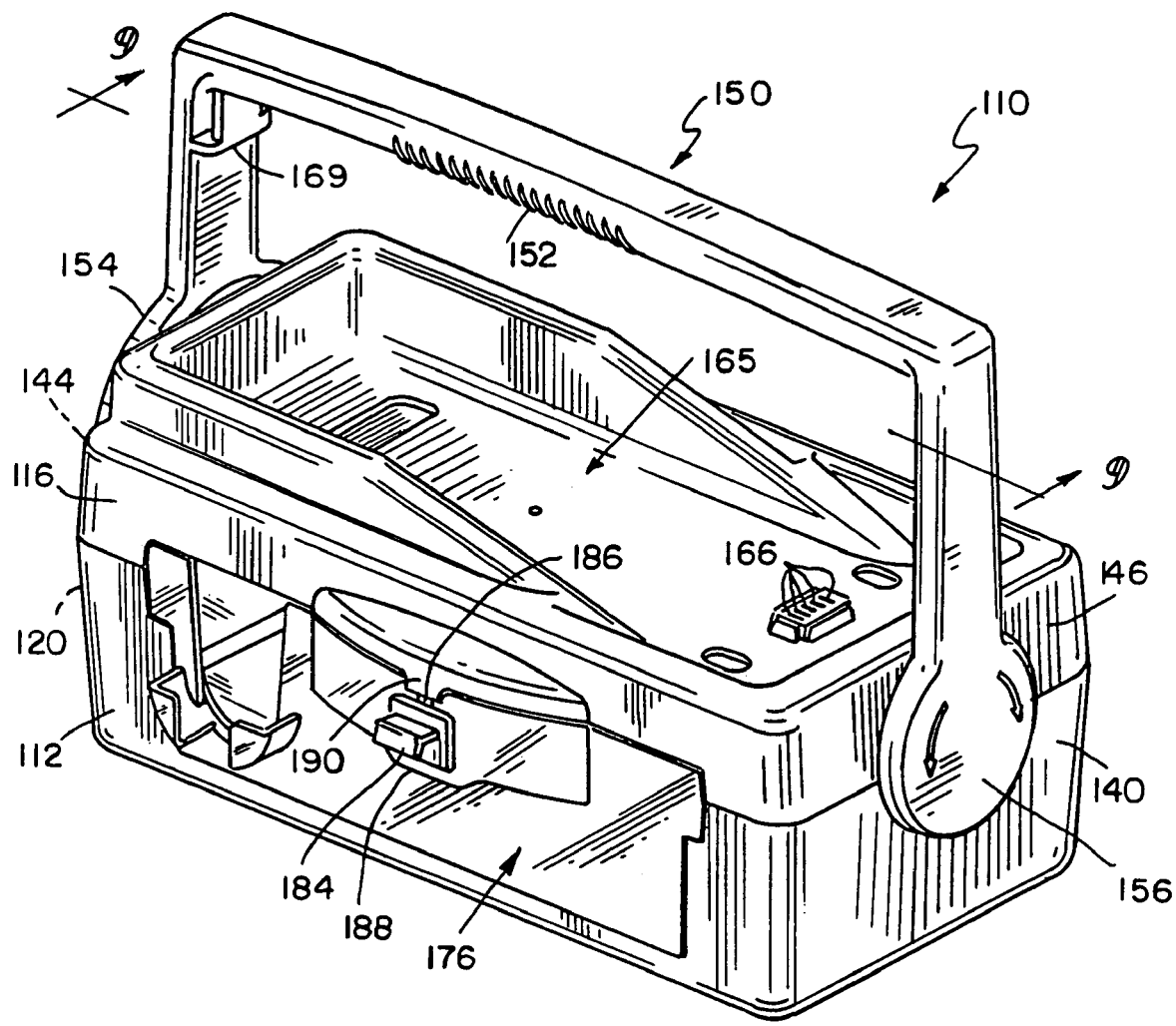
FIG. 5 illustrates a perspective view of a component of a system constructed according to the invention.
Figure 6:
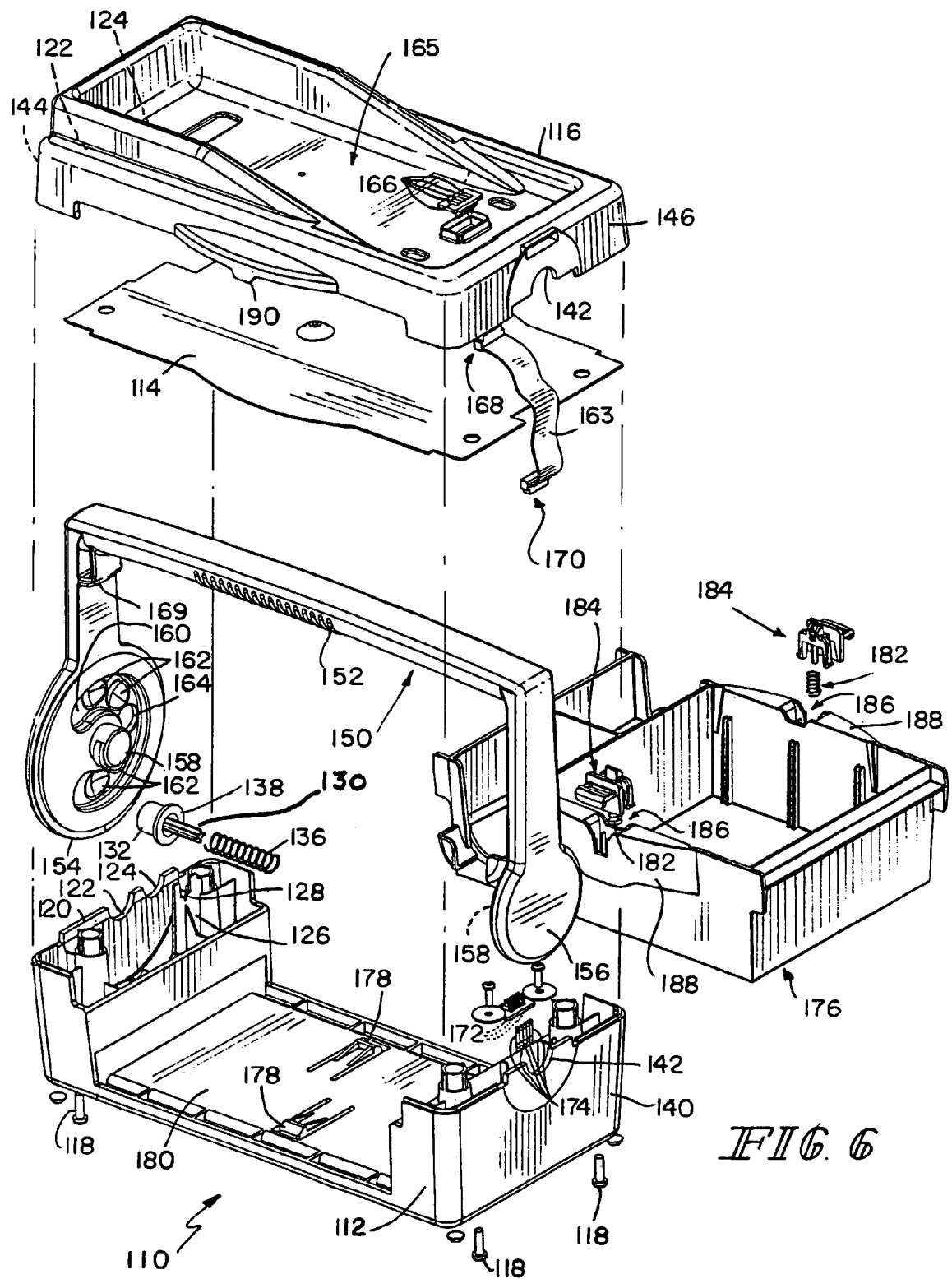
FIG. 6 illustrates a fragmentary exploded perspective view of the component illustrated in FIG. 5.

The system illustratively includes a bar code reader 52 (illustrated in phantom in FIG. 2). The bar code reader 52 has a number of different uses. For example, each patient may be provided with a bar coded patient identification tag/card and/or each operator may be provided with a bar coded operator identification tag/card. The system 20 reads the bar code labels to identify data which is downloaded into the system 20 with a particular patient and/or operator. Readings are thereby capable of being associated with a particular patient and/or with a particular operator. Illustratively, the bar code reader 52 may be factory installed into the cradle 30, or may be a field-installed addition to the cradle 30. The bar code reader 52 can include, for example, a Metrologic model MH4110 or MS4120 scan engine.

The cradle 30 includes a housing top portion 60 and a housing bottom portion 62. Housing bottom portion 62 is divided into a forward portion 64 and a separate rearward portion 66. The bar code reader 52 is housed in the rearward portion 66 and is exposed through a scan window 68 provided in the bottom of portion 66 to bar code labels 50 to be read. The batteries 44 are also housed in housing portion 66. Housing portions 62, 64, 66 illustratively are molded from filled or unfilled resins, such as, for example, an ABS-polycarbonate composite. The forward portion 64 is provided with a desired number, five in the illustrated embodiment, of probe spring contact openings 68 into which spring contact probes 70 are press fitted. One of these probes 70 is illustrated in greater detail in FIG. 7. Probes 70 illustratively include gold plated nickel silver barrels 72, gold plated hard beryllium copper plungers 74 and gold plated stainless steel springs 76. A molded-in retainer is provided at the front of bottom portion 64 to receive a front hook 78. Front hook 78 is illustrated in enlarged side elevation in FIG. 3. Its purpose will be discussed hereinafter. The rear top region of bottom portion 64 is provided with a passageway for accommodating a stylus 80 which can be used to enter data into touch screen 33 of the cradle 30.

Probes 70 are electrically connected to appropriate terminals of the circuit 45 which is provided on a circuit board 84. Circuit board 84 is mounted in the cradle 30 during the assembly of portions 62, 64. Touch screen 33 is coupled by a multi-conductor ribbon cable and complementary plug and socket to circuit board 84, and is driven by driver circuitry in circuit 45. An LCD 34/backlight 88 assembly is coupled by a multi-conductor ribbon cable and complementary plug and socket to circuit board 84, and is driven by driver circuitry in circuit 45. A threaded fastener 90 and molded ears 92 cooperating with slots 94 in housing bottom portion 64 attach housing bottom rear portion 66, with reader 52 housed therein, to housing bottom portion 64. Threaded fasteners 96 secure housing bottom portion 64 to housing top portion 62.

Housing top portion 62 is provided with a slot 98 adjacent its front surface. Front hook 78 protrudes through slot 98 above the top surface 100 of housing top portion 62. Housing top portion 62 is further provided with an opening through which LCD 34 is visible and accessible. Housing top portion 62 is also provided with a recess 102 having an overall configuration generally complementary in shape to the shape(s) of the instrument(s) 22 with which cradle 30 is designed to be used. As such, this recess 102 may be a composite of a number of different shapes, to accommodate a number of different types, styles and/or models of instruments 22. A retainer 104 snaps onto housing top portion 62 at the rearward extent of recess 102. Retainer 104 helps to retain instrument 22 in recess 102 by holding it against front hook 78. Instruments 22 are inserted into recess 102 and urged against the back wall 106 thereof, and snapped into place and held in place with the cooperation of front hook 78 and retainer 104.

Turning now to FIGS. 5–11, an accessory box 110 useful in transporting cradle 30 from place to place will be described in greater detail. Accessory box 110 includes a housing bottom portion 112 and a housing top portion 116, both of which illustratively are injection molded or otherwise formed from suitable filled or unfilled resins, and a ceiling plate 114, which illustratively is constructed from stamped metal, all held together, for example, by threaded fasteners 118. The rear region of housing bottom portion 112 includes a rear wall 120 having two upwardly opening semicircular cutouts 122, 124 formed therein. Cutout 122 is generally centered in the span of wall 120. Cutout 124 is offset to one side. A partial wall 126 extends upward from the floor of housing bottom portion 112 forward of wall 120. Partial wall 126 has a cutout 128 formed in the upper extent thereof to receive the shank 130 of a locking button 132. A coil compression spring 136 is captured on shank 130 between partial wall 126 and a collar 138 formed on button 132 to urge button 132 out of rear wall 120. Collar 138 also captures button 132 in rear wall 120.

The forward region of housing bottom portion 112 includes a forward wall 140 having an upwardly opening semicircular cutout 142 formed therein. Cutout 142 is generally centered in the span of wall 140. Housing top portion 116 includes a rear wall 144 having two downwardly opening semicircular cutouts 122, 124 complementary to cutouts 122, 124 in wall 120 formed therein, and a forward wall 146 having a downwardly opening semicircular cutout 142 complementary to cutout 142 in wall 140 formed therein. A carrying handle 150 includes a handgrip 152 and two ends 154, 156 for positioning at the back and front, respectively, of accessory box 110. Each end 154, 156 includes a pivot post 158 for engagement in a respective hole formed by a respective pair of cutouts 122, 122 and 142, 142. Pivot posts 158 are provided with retaining projections which prevent the posts 158 from disengaging from accessory box 110. One, 154, of the ends includes a circumferentially extending channel 160 for accommodating button 132. The bottom of channel 160 includes a number, illustratively four, of depressions 162 which define locking positions for handle 150, and an opening 164 which defines a central locking position of handle 150. The contours of the bottoms of depressions 162 are best illustrated in FIG. 11. As can be appreciated from FIG. 11, the contours of the bottoms of depressions 162 are smoothly curved to permit force on the handle 150 to move the handle among the positions defined by depressions 162 without damaging the handle 150 or the button 132. The depressions 162 are generally somewhat egg-shaped or elliptical in plan view to enhance this releasing characteristic of the handle 150 in these positions. The sidewalls of the central opening 164 are generally straight to permit more secure locking of handle 150 in the upright position. Opening 164 permits access to button 132 when handle 150 is in the upright position to release button 132 and permit movement of handle 150 from the upright position. When handle 150 is in the upright position and a cradle 30 is engaged in the recess 165 provided therefor on the top of accessory box 110, the cradle 30 is locked into the recess 165 by the engagement of stops 167 and 169 provided on the accessory box 110 and handle 150, respectively. The handle 150 illustratively can be made by gas assisted injection molding to make the handle 150 more robust and capable of withstanding shock, for example, during drop testing.

Probes 70 of cradle 30 make electrical contact with corresponding terminals 166 provided and positioned for this purpose on housing top portion 116 when cradle 30 is positioned in housing top portion 116. A ribbon cable 163 includes plugs 168 and 170 for making electrical contact to terminals 166 and another set of terminals 172 in the housing bottom portion 112. Terminals 172 include probes 174 of the same general configuration and mounting as probes 70 for a purpose which will be described later. Housing 110 also includes a drawer 176 which can be withdrawn from either side of housing 110. Stops 178 provided in the bottom wall 180 of housing bottom portion 112 prevent the drawer 176 from being accidentally disengaged from housing 110, regardless of from which side of housing 110 drawer 176 is withdrawn. Drawer 176 also includes spring 182-urged latches 184 which reside in wells 186 provided for latches 184 in both handles 188 of drawer 176. These latches 184 cooperate with stops 190 provided on housing top portion 116 to prevent the drawer 176 from accidentally coming open, for example, while accessory box 110 is being transported from station (for example, patient, nurses' station or the like) to station. Housing 110 components illustratively are also molded from filled or unfilled resins, such as, for example, an ABS-polycarbonate composite. Drawer 176 illustratively may be formed from a transparent or semi-transparent material such as, for example, polycarbonate.

As previously noted, the system 20 further includes base 38. Base 38 includes a third port 40 for coupling to a complementarily configured fourth port 42 on the cradle 30. Coupling of the third and fourth ports 40, 42 is achieved directly by placement of the cradle 30 directly on base 38, in which case probes 70 contact respective terminals 192 provided and positioned for this purpose on the top surface 194 of base 38. This permits downloading of data collected from instruments 22 by the cradle 30 through the base 38. Coupling of the third and fourth ports 40, 42 can also be achieved through the accessory box 110 when cradle 30 is positioned on an accessory box 110. In this case, the electrical connection is through probes 70, terminals 166, plug 168, ribbon cable 163, plug 170, terminals 172 and probes 174 to respective terminals 192 in base 38. The recess 195 in the top surface 194 of base 38 is configured to accept either cradle 30 or accessory box 110. Again, coupling of the third and fourth ports 40, 42 permits charging of batteries 44 used to power circuitry 45 in the cradle 30 through the base 38. The use of rechargeable batteries 44 reduces the requirement to change batteries. The illustrated base 38 further includes a fifth port 46 for coupling to a port 48 on computer 26 to permit the downloading of data through the base 38 to the computer 26 for storage, analysis and report generation. The bottom portion of base 38 illustratively is constructed from stamped metal and the top portion of base 38 illustratively is molded from filled or unfilled resins, such as, for example, an ABS-polycarbonate composite.

The illustrated system 20 is thus modular. The health care worker is afforded the flexibility to decide how much of the system 20 to transport to any given patient care site. For example, the worker may elect in certain instances to take only the instrument 22 itself, with entry of data and patient identification being left to be performed, for example, in part by entry through touch screen 33 or key pad, at some site remote from the patient's location, for example, at a nurses' station on a ward in a hospital. Or, for example, the worker may elect to take an instrument 22 and the cradle 30 to a patient care site, or use the cradle 30 with an instrument 22 already at a patient care site. Optionally, the worker may elect to take an instrument 22, cradle 30, and an accessory box 110 to a patient care site.

What is claimed is:

1. A healthcare data management system including an instrument for determining the concentration of a medically significant component of a body fluid, a cradle for receiving the instrument, and an accessory box for receiving the cradle, the accessory box including a housing and a carrying handle pivotally coupled to the housing, the carrying handle having two ends, one of the ends including a number of yieldable locking positions for the handle with respect to the housing.

2. The apparatus of claim 1 further including a non-yieldable locking position of the handle with respect to the housing.

3. The apparatus of claim 2 wherein the handle includes a feature for engagement with the cradle when the cradle engages the accessory box and the handle is in the non-yieldable locking position.

4. The apparatus of claim 1 wherein the accessory box includes a drawer accessible from two opposite sides of the accessory box, the drawer including a stop for reducing the likelihood of accidental disengagement of the drawer from the accessory box when the accessory box is withdrawn from either of said two opposite sides.

5. The apparatus of claim 1 wherein the accessory box includes a drawer accessible from two opposite sides of the accessory box, the drawer including latches to reduce the likelihood of inadvertent opening of the drawer.

6. The apparatus of claim 1 wherein one of the ends includes a button which is yieldably urged into engagement with one of a number of depressions which define the yieldable locking positions of the handle.

7. The apparatus of claim 6 wherein said one of the ends further includes an opening which defines a non-yieldable locking position of the handle.

8. The apparatus of claim 6 wherein the bottoms of the depressions are formed to include ramps to permit force on the handle to move the handle among the yieldable locking positions defined by the depressions.

9. The apparatus of claim 7 wherein the opening includes a sidewall which defines the non-yieldable locking position, the sidewall being configured to permit locking of the handle in the non-yieldable locking position.

10. The apparatus of claim 9 wherein the opening permits access to the button to permit movement of the handle from the non-yieldable locking position.

11. The apparatus of claim 1 wherein at least one of the handle and the cradle includes a feature for engagement with the other of the cradle and the handle when the cradle engages the accessory box and the handle is in the non-yieldable locking position.

* * * * *